(12) United States Patent
Lichter et al.

(10) Patent No.: US 12,064,170 B2
(45) Date of Patent: Aug. 20, 2024

(54) DISTAL ASSEMBLY FOR CATHETER WITH LUMENS RUNNING ALONG SPINES

(71) Applicant: Biosense Webster (Israel) Ltd., Yokneam (IL)

(72) Inventors: Justin George Lichter, Irvine, CA (US); Joseph Thomas Keyes, Sierra Madre, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 452 days.

(21) Appl. No.: 17/319,957

(22) Filed: May 13, 2021

(65) Prior Publication Data

US 2022/0361942 A1    Nov. 17, 2022

(51) Int. Cl.
  *A61B 18/14* (2006.01)
  *A61B 17/00* (2006.01)
  *A61B 18/00* (2006.01)

(52) U.S. Cl.
  CPC ............ *A61B 18/1492* (2013.01); *A61B 2017/00526* (2013.01); *A61B 2018/00267* (2013.01); *A61B 2018/00357* (2013.01); *A61B 2018/00577* (2013.01); *A61B 2018/1467* (2013.01); *A61B 2218/002* (2013.01)

(58) Field of Classification Search
  CPC ...... A61B 18/1492; A61B 2017/00526; A61B 2018/00267; A61B 2018/00357; A61B 2018/00577; A61B 2018/1467; A61B 2218/002

See application file for complete search history.

(56) References Cited

U.S. PATENT DOCUMENTS

| | | | |
|---|---|---|---|
| 4,699,147 A | 10/1987 | Chilson et al. |
| 4,940,064 A | 7/1990 | Desai |
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Extended European Search Reported dated Oct. 7, 2022, from corresponding European Application No. 22172919.7.

(Continued)

*Primary Examiner* — Linda C Dvorak
*Assistant Examiner* — Abigail Bock
(74) *Attorney, Agent, or Firm* — Troutman Pepper Hamilton Sanders LLP

(57) ABSTRACT

Medical apparatus includes an insertion tube configured for insertion into a body cavity of a patient and a distal assembly, including a plurality of spines having respective proximal ends that are connected distally to the insertion tube. Each spine includes a rib extending along a length of the spine, a flexible polymer sleeve disposed over the rib and defining a lumen running parallel to the rib along the spine, and one or more electrodes disposed on the sleeve and configured to contact tissue within the body cavity.

13 Claims, 3 Drawing Sheets

(56) References Cited

U.S. PATENT DOCUMENTS

| | | | |
|---|---|---|---|
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,443,489 A | 8/1995 | Ben-Haim | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,558,091 A | 9/1996 | Acker et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,172,499 B1 | 1/2001 | Ashe | |
| 6,216,043 B1 | 4/2001 | Swanson et al. | |
| 6,216,044 B1 | 4/2001 | Kordis | |
| 6,239,724 B1 | 5/2001 | Doron et al. | |
| 6,332,089 B1 | 12/2001 | Acker et al. | |
| 6,428,537 B1 | 8/2002 | Swanson et al. | |
| 6,456,864 B1 | 9/2002 | Swanson et al. | |
| 6,484,118 B1 | 11/2002 | Govari | |
| 6,574,492 B1 | 6/2003 | Ben-Haim et al. | |
| 6,575,997 B1 * | 6/2003 | Palmer | A61F 2/013 606/200 |
| 6,584,345 B2 | 6/2003 | Govari | |
| 6,600,948 B2 | 7/2003 | Ben-Haim et al. | |
| 6,618,612 B1 | 9/2003 | Acker et al. | |
| 6,690,963 B2 | 2/2004 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,788,967 B2 | 9/2004 | Ben-Haim et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| 7,536,218 B2 | 5/2009 | Govari et al. | |
| RE41,334 E | 5/2010 | Beatty et al. | |
| 7,756,576 B2 | 7/2010 | Levin | |
| 7,846,157 B2 | 12/2010 | Kozel | |
| 7,848,787 B2 | 12/2010 | Osadchy | |
| 7,869,865 B2 | 1/2011 | Govari et al. | |
| 7,930,018 B2 | 4/2011 | Harlev et al. | |
| 7,955,299 B2 | 6/2011 | Just et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,456,182 B2 | 6/2013 | Bar-Tal et al. | |
| 8,475,450 B2 | 7/2013 | Govari et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 * | 6/2017 | Just | A61B 18/1492 |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |
| 10,314,649 B2 | 6/2019 | Bakos et al. | |
| 10,349,855 B2 | 7/2019 | Zeidan et al. | |
| 10,350,003 B2 | 7/2019 | Weinkam et al. | |

(56) References Cited

U.S. PATENT DOCUMENTS

| | | |
|---|---|---|
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,537,286 B2 | 1/2020 | Diep et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2003/0055421 A1 | 3/2003 | West et al. |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0066316 A1* | 3/2013 | Steinke ............ A61B 18/1492 606/41 |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2013/0304062 A1 | 11/2013 | Chan |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0276733 A1 | 9/2014 | Vanscoy |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2016/0374582 A1* | 12/2016 | Wu ............ A61B 5/6859 606/41 |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0202619 A1* | 7/2017 | Lim ............ A61B 5/6858 |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319269 A1* | 11/2017 | Oliverius ............ A61B 18/1492 |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |

(56) References Cited

U.S. PATENT DOCUMENTS

| | | |
|---|---|---|
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Mswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0155224 A1 | 5/2020 | Bar-Tal |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | | |
|---|---|---|---|
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 2783651 A1 | 10/2014 | |
| EP | 2699151 B1 | 11/2015 | |
| EP | 2699152 B1 | 11/2015 | |
| EP | 2699153 B1 | 12/2015 | |
| EP | 2498706 B1 | 4/2016 | |
| EP | 2578173 B1 | 6/2017 | |
| EP | 3238645 A1 | 11/2017 | |
| EP | 2884931 B1 | 1/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3972510 A1 | 3/2022 | |
| WO | 9421167 A1 | 9/1994 | |
| WO | 9421169 A1 | 9/1994 | |
| WO | 9625095 A1 | 8/1996 | |
| WO | 9634560 A1 | 11/1996 | |
| WO | 0182814 B1 | 5/2002 | |
| WO | 2004087249 A2 | 10/2004 | |
| WO | 2004/112629 A1 | 12/2004 | |
| WO | WO-2004112629 A1 * | 12/2004 | ......... A61B 1/00087 |
| WO | WO-2005112814 A2 * | 12/2005 | ......... A61B 18/1492 |
| WO | 2012100185 A2 | 7/2012 | |
| WO | 2013052852 A1 | 4/2013 | |
| WO | 2013162884 A1 | 10/2013 | |
| WO | 2013173917 A1 | 11/2013 | |
| WO | 2013176881 A1 | 11/2013 | |
| WO | 2014176205 A1 | 10/2014 | |
| WO | 2016019760 A1 | 2/2016 | |
| WO | 2016044687 A1 | 3/2016 | |
| WO | 2018111600 A1 | 6/2018 | |
| WO | 2018191149 A1 | 10/2018 | |
| WO | 2019084442 A1 | 5/2019 | |
| WO | 2019143960 A1 | 7/2019 | |

(56) References Cited

FOREIGN PATENT DOCUMENTS

WO        2020026217 A1     2/2020
WO        2020206328 A1    10/2020

OTHER PUBLICATIONS

Shepherd G. W. et al., "Extrusion of polymer tubing using a rotating mandrel", Polymer Engineering and Science, vol. 16, No. 12, Dec. 1, 1976 (Dec. 1, 1976), pp. 827-830, XP55966335.

\* cited by examiner

DISTAL ASSEMBLY FOR CATHETER WITH LUMENS RUNNING ALONG SPINES

FIELD OF THE INVENTION

The present invention relates generally to invasive medical equipment, and particularly to apparatus for ablating tissue within the body and methods for producing such apparatus.

BACKGROUND

Cardiac arrythmias are commonly treated by ablation of myocardial tissue in order to block arrhythmogenic electrical pathways. For this purpose, a catheter is inserted through the patient's vascular system into a chamber of the heart, and an electrode or electrodes at the distal end of the catheter are brought into contact with the tissue that is to be ablated. In some cases, high-power radio-frequency (RF) electrical energy is applied to the electrodes in order to ablate the tissue thermally. Alternatively, high-voltage pulses may be applied to the electrodes in order to ablate the tissue by irreversible electroporation (IRE).

Electrical ablation, whether by RF thermal ablation or IRE, generates excess heat, which can cause collateral damage to tissues in and around the ablation site. To reduce tissue temperature and thus mitigate this sort of damage, the area of the electrodes is commonly irrigated during the ablation procedure. In some catheters, the irrigation is applied through small holes in the electrodes themselves, for example as described in U.S. Pat. No. 8,475,450, which is owned by applicant and incorporated by reference herein.

Some ablation procedures use basket catheters, in which multiple electrodes are arrayed along the spines of an expandable basket assembly at the distal end of the catheter. Various schemes have been described for irrigating such basket assemblies during ablation. For example, U.S. Pat. No. 7,955,299 describes a basket catheter with an outer tubing housing an inner fluid delivery tubing having at least one fluid delivery port. A plurality of spines are each connected at a proximal end of the spines to the outer tubing and at a distal end of the spines to the inner fluid delivery tubing. The inner fluid delivery tubing is operable to be moved in a first direction to expand the spines; and in a second direction to collapse the spines. A porous membrane is provided over at least a portion of the inner fluid delivery tubing. A seal is provided at a proximal end of the porous membrane between the porous membrane and the outer tubing and between the porous membrane and the inner fluid delivery tubing, the seal configured for irrigating between the plurality of spines of the basket catheter while preventing fluid ingress into the outer tubing.

SUMMARY

Embodiments of the present invention that are described hereinbelow provide improved apparatus for ablating tissue with the body, as well as methods for producing such apparatus.

There is therefore provided, in accordance with an embodiment of the invention, medical apparatus, including an insertion tube configured for insertion into a body cavity of a patient and a distal assembly, including a plurality of spines having respective proximal ends that are connected distally to the insertion tube. Each spine includes a rib extending along a length of the spine, a flexible polymer sleeve disposed over the rib and defining a lumen running parallel to the rib along the spine, and one or more electrodes disposed on the sleeve and configured to contact tissue within the body cavity.

In some embodiments, the spines have respective distal ends that are conjoined at a distal end of the distal assembly, and the ribs are configured to bow radially outward when the distal assembly is deployed in the body cavity, whereby the electrodes contact the tissue in the body cavity. In a disclosed embodiment, the ribs are configured to collapse radially inward so that the spines are aligned along an axis of the insertion tube while the apparatus is being inserted into the body cavity. Additionally or alternatively, the insertion tube includes a flexible catheter configured for insertion into a chamber of a heart of the patient, and the electrodes are configured to contact and apply electrical energy to myocardial tissue within the chamber.

In a disclosed embodiment, the rib includes a metal slat. Additionally or alternatively, the flexible polymer sleeve includes a thermoplastic elastomer.

In one embodiment, the lumen of each of the spines is in fluid communication with an irrigation manifold running through the insertion tube, and irrigation outlets pass through the flexible polymer sleeve to the lumen in a vicinity of the electrodes, whereby an irrigation fluid passing through the irrigation manifold exits the lumen through the irrigation outlets. Additionally or alternatively, each spine includes a wire running through the lumen and connecting electrically to at least one of the electrodes.

There is also provided, in accordance with an embodiment of the invention, a method for producing a medical device. The method includes forming a plurality of spines by, for each spine, placing a mandrel alongside a resilient rib and molding a flexible polymer sleeve over the rib and the mandrel. After molding the sleeve, the mandrel is removed so that the sleeve contains a lumen running parallel to the rib along the spine. One or more electrodes are fixed to the sleeve of each of the spines. Respective proximal ends of the spines are connected together to a distal end of an insertion tube, which is configured for insertion into a body cavity of a patient.

In a disclosed embodiment, the flexible polymer sleeve includes a thermoplastic elastomer tube, and molding the flexible polymer sleeve includes heating the thermoplastic elastomer tube to a temperature sufficient to cause the thermoplastic elastomer tube to shrink to the shape of the rib and the mandrel.

The present invention will be more fully understood from the following detailed description of the embodiments thereof, taken together with the drawings in which:

DETAILED DESCRIPTION OF EMBODIMENTS

For efficient, reliable cooling of an ablation site, it is desirable that the irrigation fluid be targeted specifically at the locations of the electrodes. In basket catheters, however, mechanical constraints and strict size limitations make it difficult to deliver the irrigation fluid along the spines to the electrodes. Although it is possible to spray irrigation fluid toward the electrodes, for example from a manifold within the basket assembly, this approach requires a high irrigation flow rate and even then may not achieve adequate cooling of the tissue.

Embodiments of the present invention that are described herein address this problem by providing methods for forming lumens along the spines of the distal assembly of a catheter, as well as assemblies containing such lumens. Spines with lumens can be formed in the disclosed manner efficiently and reliably, without substantially increasing the dimensions of the spines or altering their mechanical properties. Such lumens can be used not only for conveying irrigation fluid to the locations of the electrodes along the spines but also, additionally or alternatively, for other purposes, such as routing electrical wires along the spines. Although the embodiments described below relate specifically to basket catheters, the principles of the present invention may similarly be applied in other sorts of distal assemblies for medical probes, such as multi-arm catheters.

In the disclosed embodiments, a distal assembly of a medical probe, such as a cardiac catheter, comprises multiple spines having respective proximal ends that are connected distally to an insertion tube, which is configured for insertion into a body cavity of a patient. Each spine comprises a rib, such as a metal slat, extending along the length of the spine. A flexible polymer sleeve is disposed over the rib and defines a lumen running parallel to the rib along the spine. To create the lumen, in some embodiments, a mandrel is placed alongside the rib, the sleeve is disposed over the rib and the mandrel, and the mandrel is then removed, leaving the lumen within the sleeve. One or more electrodes are fixed externally over the sleeve so as to contact tissue within the body cavity.

Figure 1:
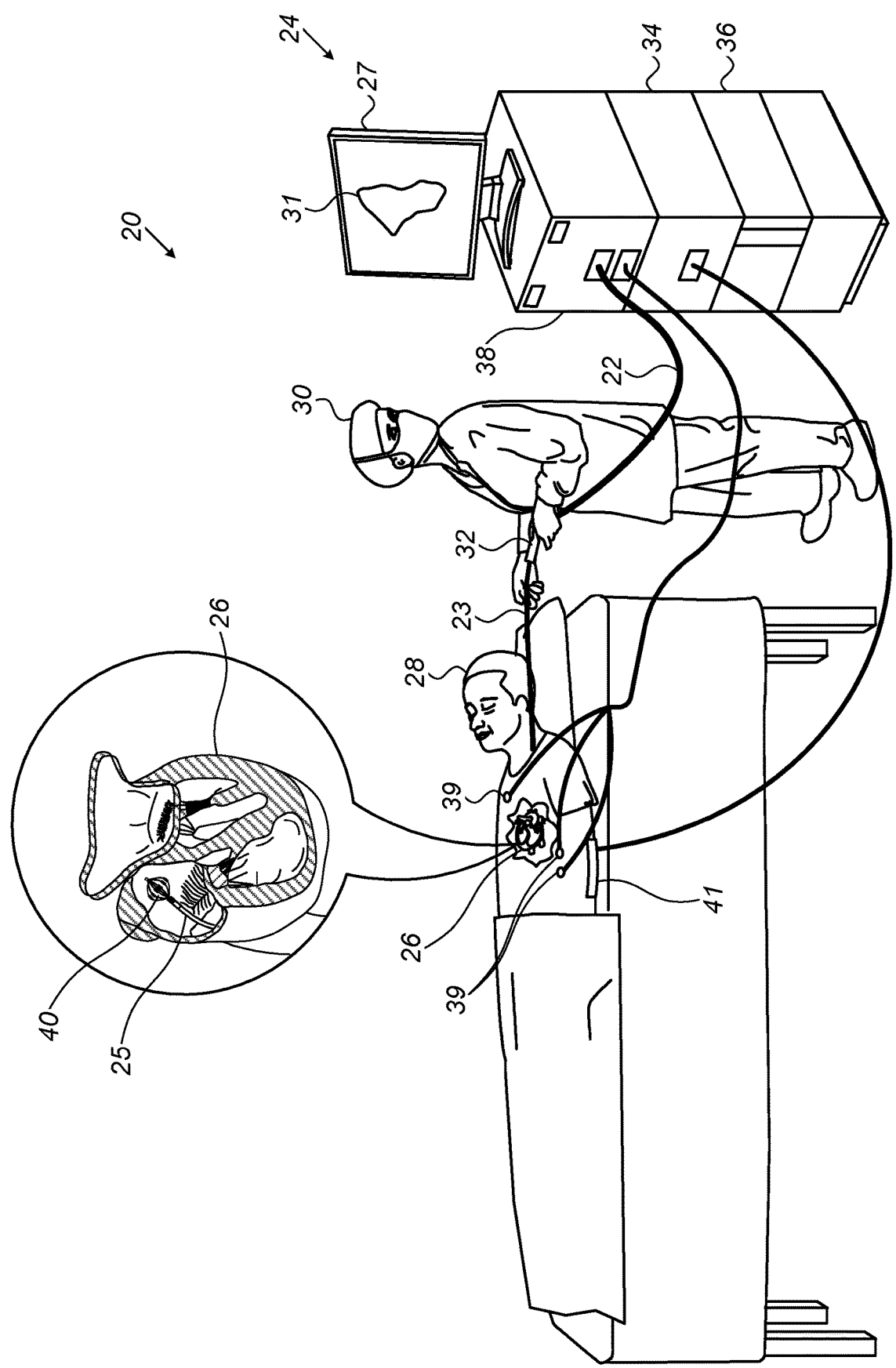
FIG. 1 is a schematic pictorial illustration showing a system for cardiac ablation, in accordance with an embodiment of the invention.

FIG. 1 is a schematic pictorial illustration of a system 20 used in an ablation procedure, in accordance with an embodiment of the invention. Elements of system 20 may be based on components of the CARTO® system, produced by Biosense Webster, Inc. (Irvine, California).

A physician 30 navigates a catheter 22 through the vascular system of a patient 28 into a chamber of a heart 26 of the patient, and then deploys a basket assembly 40 (shown in detail in FIGS. 2A/B) at the distal end of the catheter. The proximal end of basket assembly 40 is connected to the distal end of an insertion tube 25, which physician 30 steers using a manipulator 32 near the proximal end of catheter 22. Basket assembly 40 is inserted in a collapsed configuration through a sheath 23, which passes through the vascular system of patient 28 into the heart chamber where the ablation procedure is to be performed. Once inserted into the heart chamber, basket assembly 40 is deployed from the sheath and allowed to expand within the chamber. Catheter 22 is connected at its proximal end to a control console 24. A display 27 on console 24 may present a map 31 or other image of the heart chamber with an icon showing the location of basket assembly 40 in order to assist physician 30 in positioning the basket assembly at the target location for the ablation procedure.

Once basket assembly 40 is properly deployed and positioned in heart 26, physician 30 actuates an electrical signal generator 38 in console 24 to apply electrical energy (such as IRE pulses or RF waveforms) to the electrodes on the basket assembly, under the control of a processor 36. The electrical energy may be applied in a bipolar mode, between pairs of the electrodes on basket assembly 40, or in a unipolar mode, between the electrodes on basket assembly 40 and a separate common electrode, for example a conductive back patch 41, which is applied to the patient's skin. During the ablation procedure, an irrigation pump 34 delivers an irrigation fluid, such as saline solution, through insertion tube 25 to basket assembly 40.

Typically, catheter 22 comprises one or more position sensors (not shown in the figures), which output position signals that are indicative of the position (location and orientation) of basket assembly 40. For example, basket assembly 40 may incorporates one or more magnetic sensors, which output electrical signals in response to an applied magnetic field. Processor 36 receives and processes the signals in order to find the location and orientation coordinates of basket assembly 40, using techniques that are known in the art and are implemented, for example, in the above-mentioned Carto system. Alternatively or additionally, system 20 may apply other position-sensing technologies in order to find the coordinates of basket assembly 40. For example, processor 36 may sense the impedances between the electrodes on basket assembly 40 and body-surface electrodes 39, which are applied to the chest of patient 28, and may convert the impedances into location coordinates using techniques that are likewise known in the art. In any case, processor 36 uses the coordinates in displaying the location of basket assembly 40 on map 31.

Alternatively, catheter 22 and the ablation techniques that are described herein may be used without the benefit of position sensing. In such embodiments, for example, fluoroscopy and/or other imaging techniques may be used to ascertain the location of basket assembly 40 in heart 26.

The system configuration that is shown in FIG. 1 is presented by way of example for conceptual clarity in understanding the operation of embodiments of the present invention. For the sake of simplicity, FIG. 1 shows only the elements of system 20 that are specifically related to basket assembly 40 and ablation procedures using the basket assembly. The remaining elements of the system will be apparent to those skilled in the art, who will likewise understand that the principles of the present invention may be implemented in other medical therapeutic systems, using other components. All such alternative implementations are considered to be within the scope of the present invention.

Figure 2A:
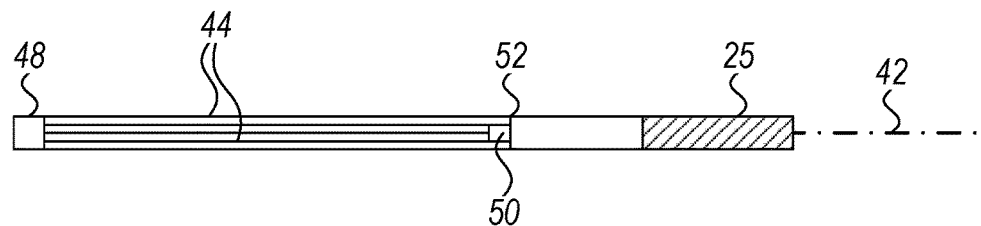
FIGS. 2A and 2B are schematic side views of a catheter basket assembly in collapsed and expanded configurations, respectively, in accordance with an embodiment of the invention.
Figure 2B:
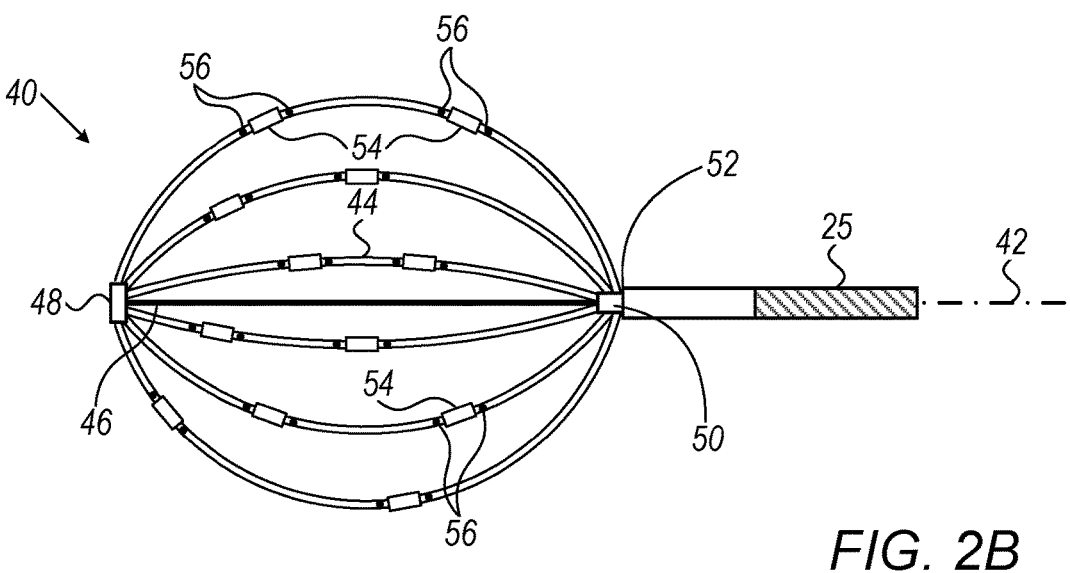

FIGS. 2A and 2B are schematic side views of basket assembly 40 in its collapsed and expanded states, respectively, in accordance with an alternative embodiment of the invention. Basket assembly 40 has a distal end 48 and a proximal end 50, which is connected to a distal end 52 of insertion tube 25. The basket assembly comprises multiple spines 44, whose proximal ends are conjoined at proximal end 50, and whose distal ends are conjoined at distal end 48. One or more electrodes 54 are disposed externally on each of spines 44. Irrigation outlets 56 in spines 44 allow irrigation fluid flowing within the spines to exit and irrigate tissue in the vicinity of electrodes 54.

In the collapsed state of FIG. 2A, spines 44 are straight and aligned parallel to a longitudinal axis 42 of insertion tube 25, to facilitate insertion of basket assembly 40 into heart 26. In the expanded state of FIG. 2B, spines 44 bow radially outward, causing electrodes 54 on spines 44 to contact tissue within the heart. In one embodiment, spines 44 are produced such that the stable state of basket assembly 40 is the collapsed state of FIG. 2A: In this case, when basket assembly 40 is pushed out of the sheath, it is expanded by drawing a puller 46, such as a suitable wire, in the proximal direction through insertion tube 25. Releasing puller 46 allows basket assembly 40 to collapse back to its collapsed state. In another embodiment, spines 44 are produced such that the stable state of basket assembly 40 is the expanded state of FIG. 2B: In this case, basket assembly 40 opens out into the expanded stated when it is pushed out of the sheath, and puller 46 may be replaced by a pusher rod to move towards a distal direction and straighten the spines 44 before the sheath is pushed distally to enclose the straightened spines.

Figure 3:
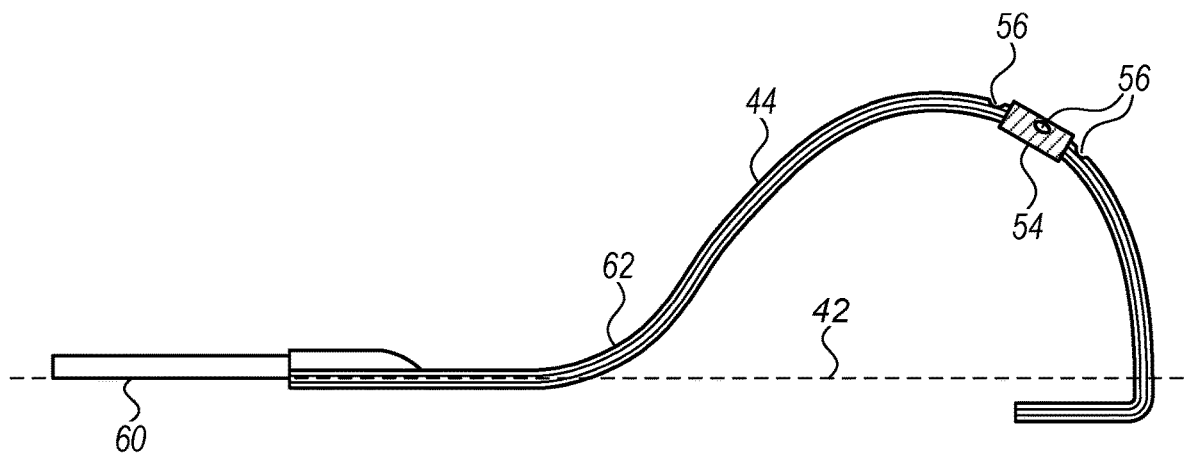
FIG. 3 is a schematic side view of a spine of a catheter basket assembly, in accordance with an embodiment of the invention.
Figure 4:
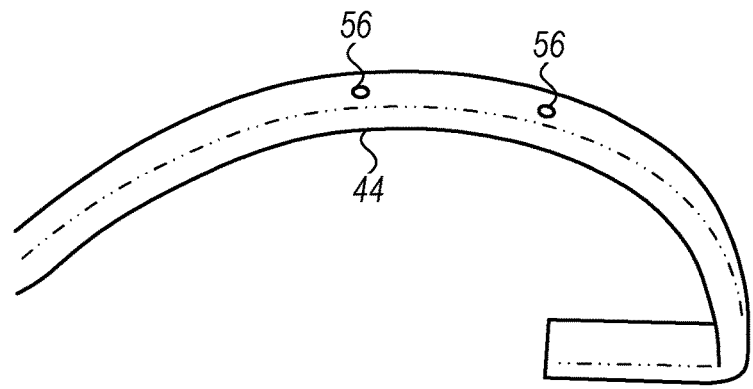
FIG. 4 is a schematic pictorial view showing details of a distal part of the spine of FIG. 3, in accordance with an embodiment of the invention.

FIGS. 3 and 4 schematically show details of one representative spine 44 in basket assembly 40, in accordance with an embodiment of the invention. FIG. 3 is a side view of spine 44, while FIG. 4 is a pictorial view of spine 44 (without the electrode 44) seen from an angle outside the basket assembly. Electrode 54 is shown in FIG. 3 between irrigation outlets 56 but is omitted from FIG. 4 for visual clarity.

As shown in FIG. 3, a lumen 62 within spine 44 is in fluid communication with an irrigation manifold 60, comprising a tube, which runs through insertion tube 25. Thus, an irrigation fluid that is pumped through irrigation manifold 60 exits lumen 62 through irrigation outlets 56. Alternatively or additionally, as noted earlier, lumen 62 may contain electrical wires 70 (shown in FIG. 7) connecting electrically to electrode 54.

Figure 5:
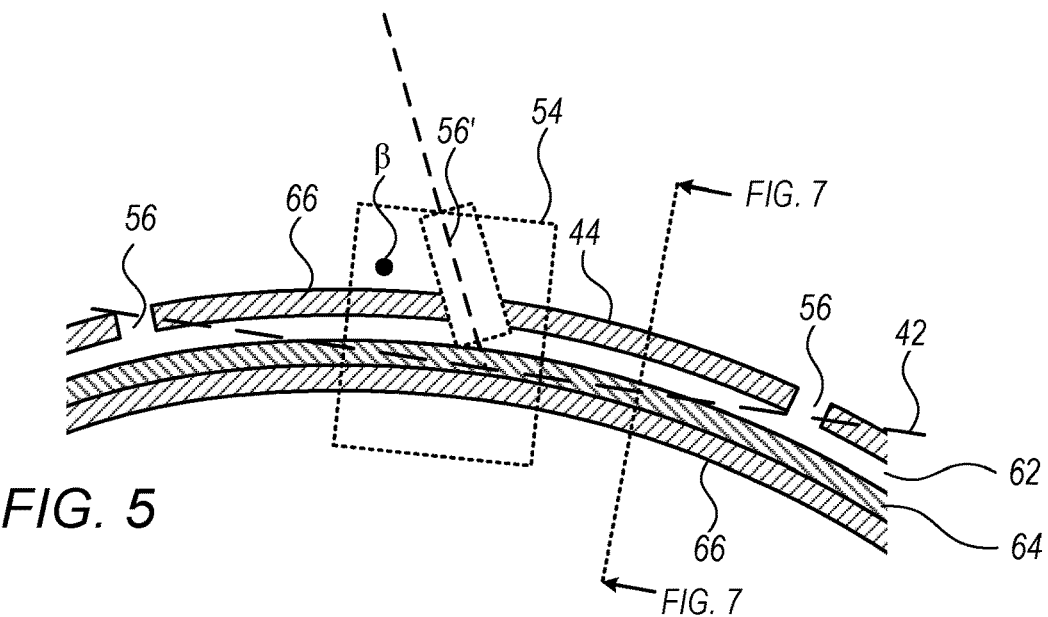
FIG. 5 is a schematic sectional view of a portion of the spine of FIG. 4 taken along a longitudinal cut, in accordance with an embodiment of the invention.
Figure 6:
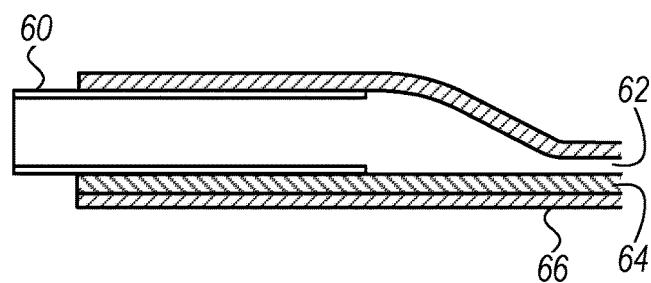
FIG. 6 is a schematic sectional view showing details of a proximal part of the spine of FIG. 3, in accordance with an embodiment of the invention.
Figure 7:
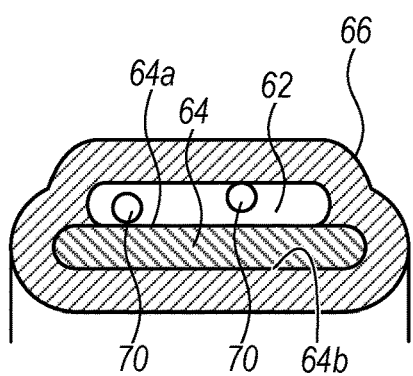
FIG. 7 is a schematic cross-sectional view of the spine of FIG. 4, in accordance with an embodiment of the invention.

Reference is now made to FIGS. 5-7, which schematically show details of the construction and method of production of spine 44, in accordance with an embodiment of the invention. FIG. 5 is a sectional view of a portion of spine 44 taken along a longitudinal cut (without the electrode 54 for clarity), while FIG. 7 is a cross-sectional view along a radial cut through the spine. FIG. 6 is a sectional view showing details of the proximal part of spine 44, including the connection of lumen 62 to irrigation manifold 60.

Spine 44 comprises a rib 64 running along the length of the spine, with a shape corresponding to the equilibrium shape of the spine. In an example embodiment, rib 64 comprises a relatively rigid slat, such as a long, thin piece of biocompatible material such as, for example, nickel titanium, having the desire curved or straight equilibrium shape. The rib 64 has a first surface 64a and an opposite surface 64b along side (e.g., parallel or non-parallel) with each other. While the embodiment in FIG. 7 shows a rectangular cross section with major side surfaces 64a and 64b, the invention is not limited to such a configuration as long as two major surfaces can be formed that run together (e.g., parallel or non-parallel) to define the slat or rib. Lumen 62 in this embodiment runs along only one of the side surfaces of rib 64, for example along surface 64a as shown in FIG. 7.

To form lumen 62, a mandrel in the shape of the lumen 62 is placed along rib 64, and a thermoplastic elastomer tube or sleeve 66 is fitted over the rib 64 and the mandrel. In one embodiment, the mandrel is made from a flexible, self-lubricating polymer with a high melting temperature, such as polytetrafluoroethylene (PTFE). The elastomer tube or sleeve 66 comprises a biocompatible material with suitable heat-shrinking properties, such as Pebax® polyether block amide shrink tubing. The elastomer sleeve 66 is mounted over rib 64 and the entire assembly is heated to a sufficient temperature to cause the elastomer tube or sleeve 66 to shrink to the shape of the underlying rib 64 and mandrel, thus forming a sleeve 66 with the sort of profile that is shown in FIG. 7. Alternatively, the rib 64 can be placed into a mold and a thermoplastic material can be used in conjunction with the mold to form sleeve 66 as a molded spine member. The mandrel inside the elastomer sleeve (or molded member) 66 is removed, leaving lumen 62 open within the sleeve 66 alongside rib 64. The distal end of the lumen 62 is sealed shut.

When lumen 62 is to be used for irrigation, manifold 60 is attached to the proximal end of the lumen 62 during the process of fabrication. Manifold 60 comprises, for example, a polyimide tube, which is tacked to the proximal end of rib 64, and the elastomer tube is fitted over the distal end of the manifold. Heating the elastomer tube causes it to shrink around manifold 60, as shown in FIG. 6, so that lumen 62 is in fluid communication with manifold 60. Holes are formed by puncturing, drilling or laser drilling through sleeve 66 into lumen 62 to create irrigation outlets 56. One or more electrodes 54 are fitted over and fastened to the outer surface of sleeve 66, for example using a suitable epoxy and/or mechanical fastener, and wires (not shown) are run between the electrodes and insertion tube 25, either along spine 44 or through lumen 62. Irrigation holes 56 can also be provided in electrode itself by forming a hole that extends through the electrode 54 and through the flexible sleeve 66 so that irrigation fluid flows through the manifold 60 through lumen 62 (of sleeve 66) and exits through irrigation hole(s) 56 in electrode 54.

It is noted that the irrigation holes 56 do not have to be at right angles to the rib 64 and can be angled from approximately 45 degrees to 135 degrees with respect to the rib 64 (or longitudinal axis 42). In FIG. 5, one exit hole 56' (on the electrode 54) is shown as being angled to allow for a desired irrigation flow pattern around the electrode contact surface with body tissue. Other permutations of this feature are within the scope of this invention. For example, the irrigation holes 56 on the sleeve 66 (not on the electrode 54) can all be angled to spray towards the electrode 54 while the irrigation hole 66 on the electrode 54 can be at a right angle to the rib 64. Alternatively, some of the irrigation holes 56 on the sleeve 66 can be angled away from electrode 54 with other irrigation holes 56' angled towards electrode 54. The electrodes 54 can be configured to have some holes 56' on the electrode 54 to flow at right angles to the rib 64 (or axis 42) and some holes 56' at an angle $\beta$ (referenced by 56' and axis 42 in FIG. 5) with respect to longitudinal axis 42.

It is noted that holes 56' may be formed through sleeve (but not through electrode 54) for the purpose of electrically connecting electrode 54 with wire(s) or conductor(s) disposed in lumen 62. The wire(s) disposed in lumen 62 can extend to a proximal handle of the device to allow for signals to flow to and from the electrode(s) 54.

After multiple spines 44 have been fabricated in this manner, the spines are grouped and joined together to form basket assembly 40, which is fixed to the distal end of insertion tube 25 as shown in FIGS. 2A/B.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
an insertion tube configured for insertion into a body cavity of a patient; and
a distal assembly extending along a longitudinal axis, comprising a plurality of spines having respective proximal ends that are connected distally to the insertion tube, each spine comprising:
a rib extending along a length of the longitudinal axis;
a flexible polymer sleeve disposed over the rib and defining:
a lumen running parallel to the rib on only one side surface of the rib; and
a plurality of irrigation outlets comprising at least a first irrigation outlet and a second irrigation outlet; and
an electrode disposed on the flexible polymer sleeve, wherein the plurality of irrigation outlets are positioned near the electrode and angled with respect to the longitudinal axis such that the first irrigation outlet is angled toward the electrode and the second irrigation outlet is angled away from the electrode.

2. The apparatus according to claim 1, wherein the spines include respective distal ends that are conjoined at a distal end of the distal assembly, and the ribs are configured to bow radially outward when the distal assembly is deployed in the body cavity, whereby the electrodes contact the tissue in the body cavity.

3. The apparatus according to claim 2, wherein ribs are configured to collapse radially inward so that the spines are aligned along an axis of the insertion tube while the apparatus is being inserted into the body cavity.

4. The apparatus according to claim 1, wherein the insertion tube comprises a flexible catheter configured for insertion into a chamber of a heart of the patient, and the electrodes are configured to contact and apply electrical energy to myocardial tissue within the chamber.

5. The apparatus according to claim 1, wherein the rib comprises a metal slat.

6. The apparatus according to claim 1, wherein the flexible polymer sleeve comprises a thermoplastic elastomer.

7. The apparatus according to claim 1, wherein the lumen of each of the spines is in fluid communication with an irrigation manifold running through the insertion tube, whereby an irrigation fluid passing through the irrigation manifold exits the lumen through the plurality of irrigation outlets.

8. The apparatus according to claim 7, wherein each spine further comprises at least one other irrigation outlet that passes through the polymer sleeve and through the electrode.

9. The apparatus according to claim 7, wherein the plurality of irrigation outlets includes at least two irrigation outlets disposed around each electrode.

10. The apparatus according to claim 9, wherein each of the irrigation outlets is angled with respect to the longitudinal axis from approximately 45 degrees to approximately 135 degrees.

11. The apparatus according to claim 1, wherein each spine comprises a wire running through the lumen and connecting electrically to the electrode.

12. The apparatus according to claim 1, wherein the irrigation outlets are angled to produce a desired irrigation flow pattern around the electrode contact surface.

13. The apparatus according to claim 8, wherein the at least one other irrigation outlet that passes through the electrode is angled at a right angle with respect to the rib.

* * * * *